US00PP13887P39

(12) United States Plant Patent

Bessho

(10) Patent No.: US PP13,887 P3

(45) Date of Patent: Jun. 17, 2003

(54) PETUNIA PLANT NAMED 'KAKEGAWA S28'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/946,089

(22) Filed: Sep. 4, 2001

(65) Prior Publication Data

US 2003/0046744 P1 Mar. 6, 2003

(51) Int. Cl.[7] ..... A01H 5/00

(52) U.S. Cl. ..... Plt./356

(58) Field of Search ..... Plt./356

(56) References Cited

PUBLICATIONS

UPOV–ROM GTITM Computer Database, 2001/06, GTI Jouve Retrieval Software, citation for 'Kakegawa S28'.*

* cited by examiner

*Primary Examiner*—Bruce R. Campell
*Assistant Examiner*—Susan B. McCormick
(74) *Attorney, Agent, or Firm*—Jondle & Associates PC

(57) ABSTRACT

A Petunia plant particularly distinguished by the dark purple flower color.

1 Drawing Sheet

GENUS AND SPECIES

*Petunia hybrida*

VARIETY DENOMINATION

'Kakegawa S28'

BACKGROUND OF THE NEW PLANT

The present invention comprises a new and distinct cultivar of Petunia, botanically known as *Petunia hybrida*, and hereinafter referred to by the cultivar name 'Kakegawa S28'. The development of 'Kakegawa S28' began with the selection of its male parent. Petunia breeding line Pg-9a-2a was crossed with breeding line 2H-1 in 1994. One $F_2$ plant from this cross was selected and then crossed to 'Surfina Violet'. This hybrid was self pollinated and selected to the $F_4$ level to produce breeding line 5BC-15A-1A-2. In 1996 this line was hybridized with Kakegawa S28's female parent, a blue-flowered petunia of dwarf habit, known as breeding line 3B-80A-1b-1a. These breeding lines are unnamed and unpatented proprietary lines. In 1997 plants from this cross were grown and observed to be segregating for habit and flower characteristics. This breeding work was performed in Kakegawa, Japan.

Two hundred $F_1$ plants from the 1996 cross were transplanted to a field in Salinas, Calif. during the summer of 1998. Seven lines were selected and vegetatively propagated for further evaluation. The seven lines were propagated again in 1999, and evaluated for fixed characteristics and ease of propagation. Final selection of one line was made during the summer of 1999. The line was established as 'Kakegawa S28', and determined to have its characteristics firmly fixed.

The terminal 1.0 to 1.5 inches of an actively growing stem was excised. The vegetative cuttings were propagated in five to six weeks. The base of the cuttings were dipped for 1 to 2 seconds in a 1:9 solution of Dip 'n Grow® (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed.

'Kakegawa S28' has been found to retain its distinctive characteristics after two years and four cycles of vegetative propagation and this novelty is firmly fixed. The variety has demonstrated stability during this time and has no inherent variation or off-types.

DESCRIPTION OF PHOTOGRAPH

This new Petunia plant is illustrated by the accompanying photograph which shows blooms, and foliage of the plant in full color, the colors shown being as true as can be reasonably obtained by conventional photographic procedures.

DESCRIPTION OF THE NEW CULTIVAR

Figure 1:
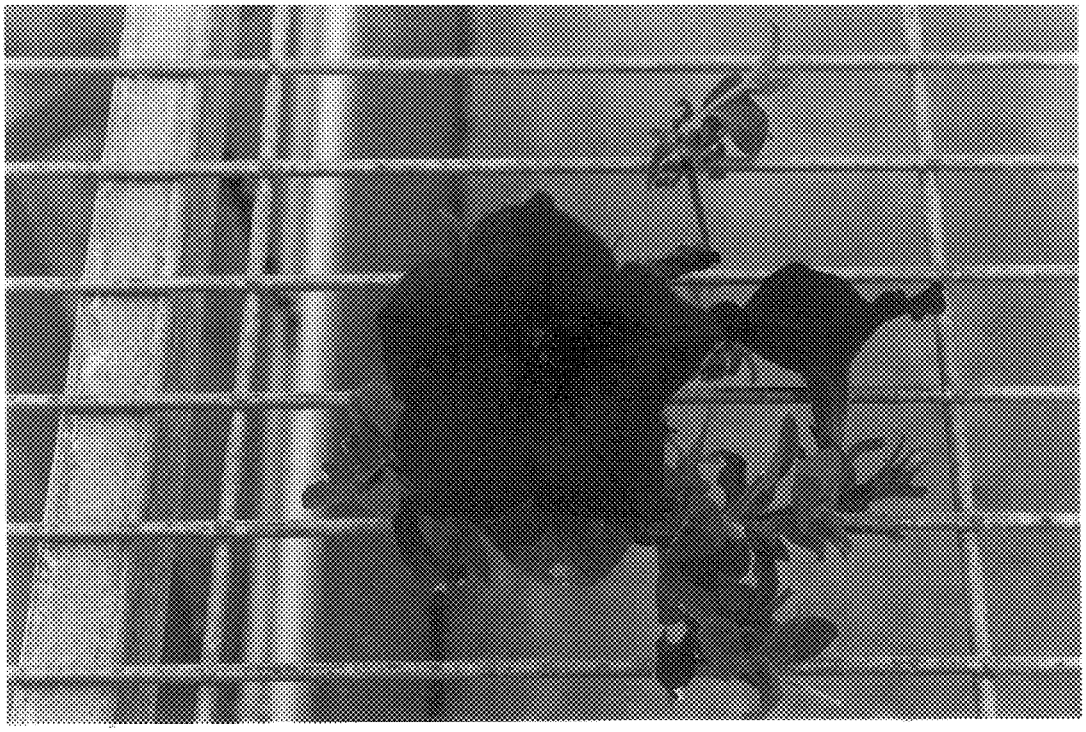
FIG. 1 shows the mature inflorescence.
Figure 2:
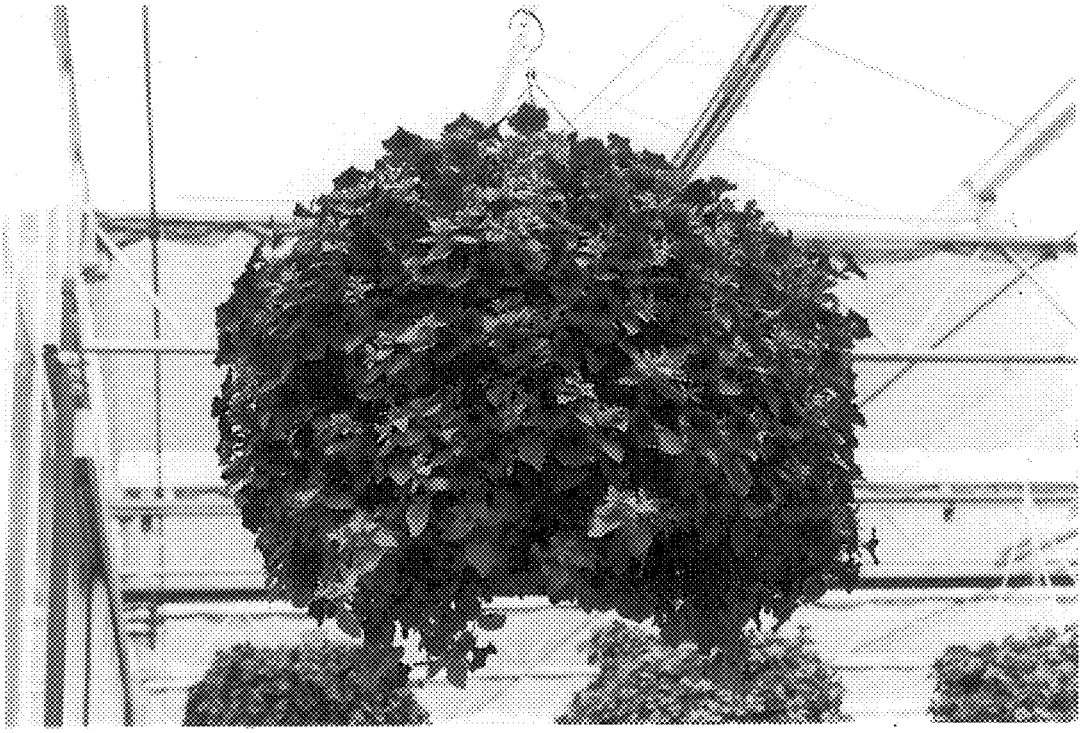
FIG. 2 shows the entire plant.

The following detailed descriptions set forth the distinctive characteristics of 'Kakegawa S28'. The data which defines these characteristics were collected from asexual reproductions carried out in Salinas, Calif. Three plants from fully rooted 15 cm diameter pots were transplanted to one 50 cm diameter hanging baskets and grown in the same conditions. Data was collected on plants in 50 cm diameter pots eight weeks after rooted cuttings were transplanted. Color references are primarily to The R.H.S. Colour Chart of The Royal Horticultural Society of London (R.H.S.).

DESCRIPTION OF THE NEW PLANT

Classification:

*Botanical.*—*Petunia hybrida.*

*Commercial.*—Petunia.

Parentage:

*Female parent.*—Breeding line 3B-80A-1b-1a.

*Male parent.*—Breeding line 5BC-15A-1A-2.

Environmental Conditions for Plant Growth

Plants were propagated from vegetative cuttings, and grown individually in 15 cm diameter plastic pots in a glass greenhouse located in Salinas, Calif. Pots contained a peat moss-based growing medium. Soluble fertilizer containing 18% nitrogen, 8% phosphorus and 18% potassium was applied in four, daily irrigations. The fifth irrigation was made with non-fertilized water. Pots were top-dressed with a slow release fertilizer containing 18% nitrogen, 8% phosphorus and 18% potassium. The typical average air temperature was 24C. The average time to initiate root development is 7 days after sticking cuttings.

Growth:

*Habit.*—Branching, mounding.

*Form.*—Descending.

*Plant size.*—91 cm total diameter and 76 cm total height when three plants are grown in a 50 cm diameter hanging basket.

*Flowering habit.*—Indeterminate.

*Time to bloom from propagation.*—4–6 weeks after rooting when grown in 10–15 cm diameter plastic pots.

*Life cycle.*—Annual.

Stems:

*Color.*—Yellow-green (RHS 145A).

*Description.*—Round, pubescent.

*Diameter.*—2–3 mm.

*Internode length.*—4 cm.

Leaves:

*Arrangement.*—Opposite.

*Apex.*—Mucronate.

*Base.*—Oblique.

*Color.*—Upper surface is green (RHS 137B) and lower surface is green (RHS 138B). Venation is yellow-green RHS 145B.

*Margin.*—Entire.

*Size.*—Length is 4.8 cm and width is 2.5 cm, both at full expansion.

*Shape.*—Ovate.

*Texture.*—Coarse.

*Venation.*—Pinnate.

*Pubescence.*—Present, clear.

*Number leaves per stem.*—Leaves occur every 4 cm; the number per stem will vary with the size of the plant.

Flowers:

*Calyx.*—5 sepals; 2 cm×8 mm (length×width).

*Corolla.*—5 petals, fused.

*Flower diameter.*—6.0–6.5 cm.

*Fragrant.*—Yes.

*Inflorescence type.*—Solitary.

*Bud.*—1.8 cm in length; 5.0 mm in diameter; color is yellow-green RHS 144C.

*Pistil.*—Compound.

*Ovary.*—Superior, parietal placentation.

*Stamens.*—5 total with two long and three short.

*Peduncle.*—2.7 cm×2 mm (length×width); pubescent.

*Petal color.*—Limbs: upper — violet-blue (RHS 89A); lower — violet (RHS 82A) with green (RHS 144C) veins. Tube: Throat— purple (RHS 77A); Inside — purple (RHS 77C) with greyed-purple (RHS 186A) veins; Outside is purple (RHS 77C) with green (RHS 144C) veins.

*Petal apex.*—Reniform.

*Petal margin.*—Smooth.

*Petal pubescence.*—Absent.

*Tube throat diameter.*—1.0 cm.

*Tube length.*—2.0 cm.

*Pollen color.*—White (RHS 155C).

*Produces seed.*—Yes; <1 mm diameter; seed coat with netted pattern; 8,000–10,000 seeds/gram; grey-orange RHS 172B.

Disease and Insect Resistance

No susceptibility to diseases or insects noted to date.

Comparison with Known Cultivars

'Kakegawa S28 ' is a distinct variety of Petunia owing to its dark purple flower color and creeping, mounding habit. 'Kakegawa S28' is most similar to the variety 'Purple Wave'; however, 'Kakegawa S28' has a darker purple flower color. Table 1 below shows the characteristics that best distinguish the new variety from the comparison variety.

TABLE 1

| Characteristic | 'Kakegawa S28' | 'Purple Wave' |
|---|---|---|
| Flower diameter | 6.0–6.5 cm | 6.2–6.7 cm |
| Primary petal color (upper) | Dark purple RHS 89A | Deep red-purple RHS 74A |
| Primary petal color (lower) | Light purple RHS 82A | Reddish purple RHS 72B |

Table 2 below shows 'Kakegawa S28' as compared to the parental varieties.

TABLE 2

| Characteristic | 'Kakegawa S28' | Pg-9a-2a | 2H-1 |
|---|---|---|---|
| Plant Habit | Semi-creeping | Erect | Creeping |
| Flower Color | Dark purple | Dark blue | Magenta |
| Stem Anthocyanin | Absent | Unknown | Absent |
| Leaf Shape | Ovate | Unknown | Ovate |

I claim:

1. A new and distinct Petunia plant as shown and described herein.

* * * * *